United States Patent
Crane

(10) Patent No.: US 9,167,998 B2
(45) Date of Patent: Oct. 27, 2015

(54) METHODS AND SYSTEMS FOR TREATMENT OF VESTIBULAR DISORDERS

(75) Inventor: Benjamin T. Crane, Pittsford, NY (US)

(73) Assignee: University of Rochester, Rochester, NY (US)

(*) Notice: Subject to any disclaimer, the term of this patent is extended or adjusted under 35 U.S.C. 154(b) by 617 days.

(21) Appl. No.: 13/405,202

(22) Filed: Feb. 24, 2012

(65) Prior Publication Data

US 2012/0218285 A1 Aug. 30, 2012

Related U.S. Application Data

(60) Provisional application No. 61/446,994, filed on Feb. 25, 2011.

(51) Int. Cl.
*A61B 5/11* (2006.01)
*A61B 5/00* (2006.01)
*G06T 11/00* (2006.01)

(52) U.S. Cl.
CPC ........... *A61B 5/4023* (2013.01); *G06T 11/00* (2013.01); *A61B 5/1114* (2013.01); *A61B 5/6803* (2013.01); *A61B 2562/0219* (2013.01); *G09G 2320/0261* (2013.01); *G09G 2380/08* (2013.01)

(58) Field of Classification Search
CPC ....... G06T 1/001; G06T 11/001; G06T 11/60; G06T 15/005; G06T 19/00; G06T 11/00; A61B 3/08; A61B 3/032; A61B 3/02; A61B 5/4023; A61B 5/6803; A61B 5/1114; G09G 2320/0261; G09G 2380/08
USPC ............... 345/418, 619; 351/201, 224, 210; 600/558, 544; 607/45; 128/898; 8/115.51
See application file for complete search history.

(56) References Cited

U.S. PATENT DOCUMENTS

| | | | | |
|---|---|---|---|---|
| 2004/0006827 | A1* | 1/2004 | Rising | 8/115.51 |
| 2006/0005846 | A1* | 1/2006 | Krueger et al. | 128/898 |
| 2006/0235331 | A1* | 10/2006 | Kiderman | 600/558 |
| 2007/0121066 | A1* | 5/2007 | Nashner | 351/210 |
| 2008/0151192 | A1* | 6/2008 | Wood et al. | 351/224 |
| 2009/0024050 | A1* | 1/2009 | Jung et al. | 600/544 |
| 2009/0326604 | A1* | 12/2009 | Tyler et al. | 607/45 |
| 2012/0307203 | A1* | 12/2012 | Vendel et al. | 351/201 |

OTHER PUBLICATIONS

Healey, Christopher et al., "Perception in Visualization", http://www.csc.ncsu.edu/faculty/healey/PP/, May 2009.*

(Continued)

*Primary Examiner* — Chante Harrison
(74) *Attorney, Agent, or Firm* — McDermott Will & Emery LP

(57) ABSTRACT

Methods and systems for assessing and treating vestibular disorders can include displaying a graphic and providing relative movement between the graphic and a user's head. Information can be obtained either directly or indirectly from the user regarding her perception of the graphic. A graphic display parameter and/or a relative movement parameter can be modified in response to the information regarding the user's perception. An indicator of the user's ability to perceive the graphic can be generated through a series of iterations. A graphic display parameter and/or a relative movement parameter for use in a subsequent series of iterations can be modified based at least in part on the indicator.

7 Claims, 11 Drawing Sheets

(56) References Cited

OTHER PUBLICATIONS

Asai, et al., *Subclinical deviation of the subjective visual vertical in patients affected by a primary headache*. Acta Otolaryngol, 2009. 129(1): p. 30-5.

Bronstein, A.M., *The interaction of otolith and proprioceptive information in the perception of verticality. The effects of labyrinthine and CNS disease*. Ann N Y Acad Sci, 1999. 871: p. 324-33.

Chang, C.P. and T.C. Hain, *A theory for treating dizziness due to optical flow (visual vertigo)*. Cyberpsychol Behav, 2008. 11(4): p. 495-8.

Conforto, A, et al., *Migraine and motion sickness independently contribute to visual discomfort*. Cephalalgia, 2009.

Dichgans, J., et al., *Moving visual scenes influence the apparent direction of gravity*. Science, 1972. 178(66): p. 1217-9.

Drummond, P.D., *Triggers of motion sickness in migraine sufferers*. Headache, 2005. 45(6): p. 653-6.

Friedmann, G., *The influence of unilateral labyrinthectomy on orientation in space*. Acta Otolaryngol, 1971. 71(4): p. 289-98.

Furman, J.M. and D.A. Marcus, *A pilot study of rizatriptan and visually-induced motion sickness in migraineurs*. Int J Med Sci, 2009. 6(4): p. 212-7.

Gottshall, K.R., R.J. Moore, and M.E. Hoffer, *Vestibular rehabilitation for migraine-associated dizziness*. Int Tinnitus J, 2005. 11(1): p. 81-4.

Guerraz, M., D. Poquin, and T. Ohlmann, *The role of head-centric spatial reference with a static and kinetic visual disturbance*. Percept Psychophys, 1998. 60(2): p. 287-95.

Hughes, P.C., G.A. Brecher, and S.M. Fishkin, *Effects of rotating backgrounds upon the perception of verticality*. Percept Psychophys, 1972. 11: p. 135-38.

Kayan, A and J.D. Hood, *Neuro-otological manifestations of migraine*. Brain, 1984. 107 (Pt 4): p. 1123-42.

Lopez, C., et al., *Changes of visual vertical perception: a long-term sign of unilateral and bilateral vestibular loss*. Neuropsychologia, 2007. 45(9): p. 2025-37.

Marcus, D.A. and M. J. Soso, *Migraine and stripe-induced visual discomfort*. Arch Neurol, 1989. 46(10): p. 1129-32.

Marcus, D.A., S.L. Whitney, and J.M. Furman, *Treatment of migrainous vertigo*. Expert Rev Neurother, 2003. 3(3): p. 307-16.

McKendrick, A.M., et al., *Motion perception in migraineurs: abnormalities are not related to attention*. Cephalalgia, 2006. 26(9): p. 1131-6.

Norre, M.E. and W. De Weerdt, *Treatment of vertigo based on habituation. 2. Technique and results of habituation training*. J Laryngol Otol, 1980. 94(9): p. 971-7.

Norre, M.E. and W. De Weerdt, *Treatment of vertigo based on habituation. 1. Physio-pathological basis*. J. Laryngol Otol, 1980. 94(7): p. 689-96.

Pavlou, M., et al., *Simulator based rehabilitation in refractory dizziness*. J Neurol, 2004. 251 (8): p. 983-95.

Vibert, D. and R. Hausler, *Long-term evolution of subjective visual vertical after vestibular neurectomy and labyrinthectomy*. Acta Otolaryngol, 2000. 120(5): p. 620-2.

Viirre, E. and R. Sitarz, *Vestibular rehabilitation using visual displays: preliminary study*. Laryngoscope, 2002. 112(3): p. 500-3.

Vitte, E., A. Semont, and A. Berthoz, *Repeated optokinetic stimulation in conditions of active standing facilitates recovery from vestibular deficits*. Exp Brain Res, 1994. 102( 1): p. 141-8.

Whitney, S.L., et al., *Physical therapy for migraine-related vestibulopathy and vestibular dysfunction with history of migraine*. Laryngoscope, 2000. 110(9): p. 1528-34.

Whitney, S.L., et al., *Responses to a virtual reality grocery store in persons with and without vestibular dysfunction*. Cyberpsychol Behav, 2006. 9(2): p. 152-6.

Witkin, H.A. and S.E. Asch, *Studies in space orientation; further experiments on perception of the upright with displaced visual fields*. J Exp Psychol, 1948. 38(6): p. 762-82.

Wrisley, D.M., S.L. Whitney, and J.M. Furman, *Vestibular rehabilitation outcomes in patients with a history of migraine*. Otol Neurotol, 2002. 23(4): p. 483-7.

Vorteq Active Head Rotation & DVA-T Dynamic Visual Acuity Test, Micromedical Technologies brochure, Apr. 2008.

Visual Eyes VNG/ENG Micromedical Technologies brochure, Sep. 2010.

System 2000 Rotational Vestibular Chair, Micromedical Technologies brochure, Sep. 2010.

System 2000 Reclining Rotational Vestibular Chair, Micromedical Technologies brochure, Sep. 2011.

\* cited by examiner

System 300

METHODS AND SYSTEMS FOR TREATMENT OF VESTIBULAR DISORDERS

RELATED APPLICATIONS

This application claims the benefit of U.S. Provisional Application Ser. No. 61/446,994, filed on Feb. 25, 2011, and titled METHODS AND SYSTEMS FOR VERTIGO TREATMENT, the entirety of which is hereby incorporated by reference.

FIELD

The present disclosure generally relates to treatment of vestibular disorders, such as those that may produce vertigo for example, and more particularly to methods and systems for treating vestibular disorders using visual image, such as a displayed graphic for example.

BACKGROUND

Disorders of the vestibular system present important clinical problems. Dizziness, a term which can embrace imbalance, vertigo, and light-headedness, affects more than 20% of the working age population, bedside tests suggest vestibular disorders in 35% of those over 40, and the prevalence is greater than 60% in the elderly. Using a more strict definition of vertigo, a prevalence of 7.4% was suggested, 80% of who seek medical consultation. Disorders of balance can be classified into one of two major categories: central vestibular disorders (i.e., disorders of the brain and central nervous system) and peripheral vestibular disorders (disease of the inner ear and eighth cranial nerve).

Migraine is one of the most common central disorders associated with vertigo, producing dizziness symptoms in 3.2% of the population. Of those who consult a physician for these symptoms, only 20% are correctly diagnosed, and fewer are appropriately treated. Vestibular disorders are likely poorly identified due to physician training and limitations in current vestibular tests. There are currently several names used in the literature to describe vertigo due to migraine, including migrainous vertigo, migraine associated dizziness, and chronic subjective dizziness. This document refers to all of these as migraine associated vertigo (MAV). Despite being very common, MAV is difficult to diagnose, due to controversy in what diagnostic criteria should be used and current lack of any diagnostic test.

SUMMARY

The disclosed systems and methods in certain embodiments allow vestibular disorders, such those that may produce as vertigo for example, to be treated by simulating movement. For example, for users suffering from MAV, peripheral vestibular hypofunction (PVH), or other vestibular disorders, information about the user's perception of the simulated movement allows the simulation to be modified to a level appropriate for the individual user.

In certain embodiments, a method for a vestibular disorder can comprise displaying a graphic and prompting relative movement between the graphic and a user's head. The method further includes obtaining information regarding the user's perception of the graphic. The method further includes modifying, responsive to the obtained information, at least one of a graphic display parameter and a relative movement parameter. The method includes repeating the displaying, prompting, obtaining, and modifying in a first series of iterations, with at least one of the displaying and prompting being performed, based at least in part on the modified at least one of the graphic display parameter and the relative movement parameter, to generate a first indicator of the user's perception of the graphic. At least approximately one day after conclusion of the first series, the displaying, prompting, obtaining, and modifying are repeated in a second series of iterations. Performance of at least one of the displaying and the prompting in the second series is based at least in part on the first indicator.

In certain embodiments, the graphic includes a dynamic image and a static image and the user's head remains static. The perception information includes an indication of perceived orientation of the static image. The dynamic image can rotate and the static image can include a representation of a line. The perceived orientation indication includes an indication that the representation of the line is perceived as either vertical, rotated in a first direction from vertical, or rotated in a second direction from vertical.

In certain embodiments, the method includes permitting movement of the user's head, so as to provide the relative movement between the graphic and the user's head, and determining whether the user's head movement exceeds a threshold. Only if the user's head movement exceeds the threshold, the graphic is displayed to the user. The threshold can be selected on the perception information of a previously displayed graphic, and can include minimum velocity, minimum frequency, and/or minimum amplitude of head movement. The graphic can include a static optotype and the perception information can include an indication of perceived orientation of the optotype. The optotype can include a ring with a gap and the indication of perceived orientation can include an indication of perceived direction of the gap.

In certain embodiments, a system for treating a vestibular disorder can comprise a display module, a movement module, a perception module, and a modification module. The display module is configured to facilitate, by a processor, displaying a graphic. The movement module is configured to facilitate, by a processor, providing relative movement between the graphic and a user's head. The perception module is configured to receive, by a processor, information regarding the user's perception of the graphic. The modification module is configured to configured (a) to facilitate, by a processor and responsive to the obtained information, modifying at least one of a graphic display parameter and a relative movement parameter, (b) to facilitate, by a processor and based on the obtained information, generating at least a first indicator of the user's perception of the graphic and modifying, based at least in part on the first indicator, at least one of (i) a graphic display parameter affecting the displaying of the graphic at least approximately one day after generation of the first indicator and (ii) a relative movement parameter affecting the prompting of relative movement at least approximately one day after generation of the first indicator. The system can further include a computer display configured to display the graphic, and a user interface configured to receive the information indicative of the user's perception of the graphic. The user interface can include a keyboard, a computer mouse, a button, and/or a joystick among other devices.

In certain embodiments, the graphic includes a dynamic image and a static image and the perception information includes an indication of perceived orientation of the static image. The dynamic image can rotate and the static image can include a representation of a line. The perceived orientation indication includes an indication that the representation of the line is perceived as either vertical, rotated in a first direction from vertical, or rotated in a second direction from vertical.

In certain embodiments, the system further includes a headgear module. The headgear module is configured to facilitate, by a processor, requesting movement of the user's head, so as to provide the relative movement between the graphic and the user's head. The headgear module is further configured to receive, by a processor, information regarding movement of the user's head. The headgear module is also configured to facilitate, by a processor, determining whether the user's head movement exceeds a threshold. Responsive to the obtained information, the headgear module is configured to facilitate, by a processor, displaying the graphic only when the user's head movement exceeds the threshold. The threshold can be selected on the perception information of a previously displayed graphic, and can include minimum velocity, minimum frequency, and/or minimum amplitude of head movement. The graphic can include a static optotype and the perception information can include an indication of perceived orientation of the optotype. The optotype can include a ring with a gap and the indication of perceived orientation can include an indication of perceived direction of the gap.

In certain embodiments, a machine-readable storage medium includes machine-readable instructions for causing a processor to execute a method for treating a vestibular disorder. The method includes instructions including code for displaying a graphic and for prompting relative movement between the graphic and a user's head. The instructions further include code for obtaining information regarding the user's perception of the graphic. The instructions also include code for modifying, responsive to the obtained information, at least one of a graphic display parameter and a relative movement parameter. The instructions also include code for repeating the displaying, prompting, obtaining, and modifying in a first series of iterations, with at least one of the displaying and prompting being performed, based at least in part on the modified at least one of the graphic display parameter and the relative movement parameter, to generate a first indicator of the user's perception of the graphic. The instructions also include code for repeating, at least approximately one day after conclusion of the first series, the displaying, prompting, obtaining, and modifying in a second series of iterations. The instructions further include code for performing at least one of the displaying and the prompting in the second series is based at least in part on the first indicator.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments.

DETAILED DESCRIPTION

Figure 1:
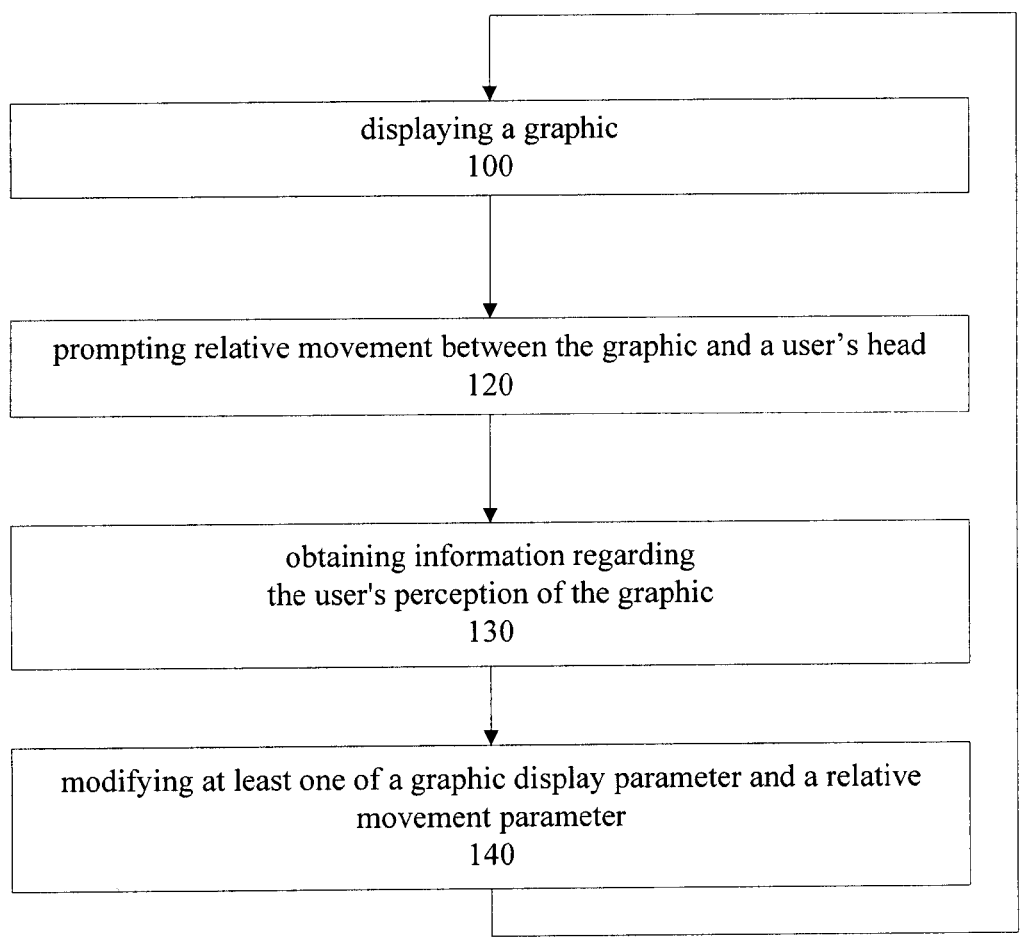
FIG. 1 illustrates an exemplary method for treating vertigo using a displayed graphic.

One method of assessing vestibular perception is subjective visual vertical (SVV), or having subjects orient a bar with their perception of vertical. Deviation towards the ablated side occurs in acute unilateral vestibular loss. However, tilt perception is a static phenomenon which, unlike vertigo, is rarely clinical significant.

The visual background also effects SVV. For instance, a static visual scene that is tilted with respect to gravity will cause a shift in SVV. With a rotating background, the SVV task becomes dynamic visual vertical (DVV), which is normally shifted in the direction of rotation.

Visual motion sensitivity can be used as a clinical test. Immediately after an acute vestibular deafferentation, both SVV and DVV are shifted towards the lesion side. With time the SVV recovers, as does the DVV when roll is towards the lesioned side. However, the normal shift in DVV with a roll stimulus is no longer observed in the contralesional direction, and this effect persists for at least a year after the lesion. This phenomenon can form a basis of an easily administered test of unilateral otolith function. It also raises the issue of vestibular function affecting visual perception. The shift in DVV is greatly exaggerated with bilateral vestibular loss. Central disturbances also influence DVV including migraine headache. Although abnormalities in SVV and DVV have been reported in clinical populations, investigation of these phenomena as a diagnostic test and comparison with other clinical measures such as the dizziness handicap inventory (DHI) has not been performed, nor has the potential effects of training.

MAV is a common cause of vertigo, with symptoms including sensitivity to actual motion, visual motion, and caloric stimulation. Visual motion perception in MAV demonstrated impaired motion direction detection and discomfort with moving patterns. The sensitivity to visual motion has diagnostic value in migraine. Visual motion sensitivity has been employed to assess migraine treatment efficacy. Motion sensitivity with visual patterns correlates with the migraine severity, suggesting a mechanism to monitor treatment, although the severity of motion sensitivity has not been correlated with established clinical tests. In addition to these, there are further shortcomings in prior studies, which warranted further study of this effect. First, patient selection used migraine headache criteria rather than MAV. Second, when MAV patients are selected, the patient inclusion criteria are often vague. Although standardized criteria for MAV have been proposed, there remains debate as to what criteria are appropriate.

Other vestibular disorders, such as peripheral vestibular hypofunction (PVH) for example, also can cause vertigo. Peripheral vestibular disorders are also common. Vestibular hypofunction can occur due to exposure to drugs such as gentamicin, streptomycin, and some chemotherapy agents.

Unilateral peripheral vestibular dysfunction can occur due to Meniere's Disease, vestibular schwannomas, trauma, vestibular neuronitis, aging, or idiopathic causes. Peripheral vestibular dysfunction can be diagnosed using caloric irrigation first described by Robert Barany almost a century ago, by measuring dynamic visual acuity, or other tests such as the head thrust test.

There is currently no medication or surgery that can improve peripheral vestibular function. This is a serious problem to society because decline of vestibular hypofunction commonly occurs with advancing age and has been implicated in 80% of falls that result in Emergency Department visits in the elderly. Such falls result in significant morbidity and health care expense.

One symptom that can occur due to vestibular hypofunction is oscillopsia or the perception that vision is not stable with head motion. This symptom is more rare than vestibular hypofunction because patients will often adjust for their hypofunction by decreasing their head motion.

A test of vestibular function based on this principle is dynamic visual acuity (DVA). The patient's static visual acuity (SVA) can be measured with the head stationary and, in some instances, prior to testing DVA. During the DVA test patients are encouraged to move their head back and forth while viewing visual optotypes. In the simplest version of the test patients view a Snellen chart (a standard visual acuity chart found in many physicians offices). However, the test is not considered accurate unless the head movement can be controlled with blanking of the visual optotypes when the head is moving at lower than the target velocity because subjects will subconsciously "cheat" by decreasing their head velocity until the optotype is clearly visible. There are currently commercially available devices that monitor head velocity, and display a visual optotype on a screen when head velocity is higher than a threshold, to measure DVA as a test of vestibular function.

Current treatment for vestibular hypofunction is focused predominately around a form of physical therapy known as vestibular rehabilitation. The mainstay of vestibular therapy is encouraging exercises which combine head movement with visual feedback, this trains the central nervous system to appropriately recalibrate the remaining vestibular function and make use of other cues such as proprioception. Exercises include telling the patient to rotate their head from side to side while focusing on a visual target such as fine print in a book. Although this improves vestibular function over time, patients often do not realize they are improving because they tend to adjust the velocity of their head movement to a level where they can see the visual cue.

Visual motion exposure can be useful as a rehabilitation strategy. The mainstay of vestibular rehabilitation is habituation to actual motion. Vestibular rehabilitation has been shown to be beneficial for MAV, although improvement is less than that achieved with peripheral vestibulopathy. It may be that standard vestibular rehabilitation paradigms are not ideal for patients with MAV, and it has also been difficult to monitor patient compliance with vestibular rehabilitation exercises. Manipulation of the visual surroundings has been reported as an alternate rehabilitation strategy and patients with visual vertigo receiving such a therapy improved more than with traditional vestibular rehabilitation. However, these studies have not examined the potential value of progressively modulating the visual motion stimulus. A recent case report has shown slowly increasing visual motion has rehabilitation potential in migraine, but the potential benefit of such a strategy needs to be studied in a larger population in a controlled manner.

Patients with MAV often experience exacerbated dizzy symptoms with visual motion stimuli even when the head is stationary. Motion on computer screens is often bothersome to these patients and can be debilitating due to the ubiquity of computers in modern society. Measuring perception of visual motion on computer screens can be used as a diagnostic test and gradual habituation to such stimuli over time can be of therapeutic benefit.

Rotating visual stimuli are poorly tolerated in MAV patients and will cause greater than normal DVV deviation. Performance on this task can be correlated with symptom severity using validated measures such as the dizziness handicap inventory (DHI). Asking patients to grade the severity of their discomfort at viewing such stimuli or their ability to view them also can be of diagnostic benefit.

In the following detailed description, numerous specific details are set forth to provide a full understanding of the present disclosure. It will be apparent, however, to one ordinarily skilled in the art that the embodiments of the present disclosure can be practiced without some of these specific details. In other instances, well-known structures and techniques have not been shown in detail so as not to obscure the disclosure.

Described herein are systems and methods for treatment of vestibular disorders, such as those that may produce vertigo for example, using a visual image such as a displayed graphic for example. As used herein, the term "graphic" is not restricted to a particular instance or presentation of a particular visual image; rather, "graphic" as used herein includes a collection, class, and/or category of parameters and/or attributes that are descriptive and/or characteristic of a visual image that may comprise one or more elements, any or all of which may or may not be presented or displayed at any given time.

Referring to FIG. 1, various methods for treating a vestibular disorder can include generating a graphic 100. The method can include prompting relative movement between a graphic and a user's head 120. The relative movement can be provided while the user views the graphic. In some embodiments, the relative movement can be sufficient to induce vertigo symptoms in the user. The method can include obtaining information regarding the user's perception of the graphic 130. Once information regarding the user's perception of the graphic has been obtained, and responsive to the obtained information, the method can include modifying at least one of a display parameter and a relative movement parameter 140. Responsive to the obtained information, the method can include repeating various steps, such as, for example, generating the display output 100, providing relative movement between the graphic and the user's head 120, and obtaining information regarding the user's perception of the graphic 130.

The graphic displayed at step 100 can be displayed in any of a number of ways. In some embodiments, the graphic can be displayed at or by a display unit. The display unit can be, for example, a computer display, a mobile phone display, a tablet display, or a television display. The graphic can be displayed on a screen, such as a computer, mobile phone, tablet, or television screen, or as an image otherwise projected or displayed on a surface. The graphic can comprise multiple features including text, such as instructions, and symbols, such as optotypes. Although the graphic is shown as step 100 in FIG. 1, the display of the graphic can continue and change during some of the disclosed methods, including during performance of other steps. For example, in some embodiments, the graphic can be presented initially as a black screen and subsequently modified to include text, symbols, or both. Displayed text and symbols can be modified during the display.

The relative movement prompted at step 120 can be any movement or perceived movement between the graphic and the user's head. In various embodiments, the relative movement between the graphic and the user's head can be prompted while all or a portion of the graphic is not visible to the user. In some embodiments, the relative movement can be any visual image tending to induce vertigo symptoms in the user. For example, the movement can include rotational movement of the graphic about a point or an axis within the user's field of vision. Alternatively, or additionally, the movement can include movement of the user's head in any of a number of manners, including side-to-side motion, up-and-down motion, and any other type of head motion. Side-to-side motion can be provided by rotation of the head about a generally vertical axis when the user is standing or seated generally upright. Up-and-down motion, can be provided by rotation of the head about a generally horizontal axis when the user is standing or seated generally upright. Although the nature of the motion has been described with reference to the user being in a standing or generally upright seated position, the similar motion of the head relative to the body can be provided with the user in a partially or fully reclined position. When the head is moved relative to the graphic, the user's head can move relative to the user's body or the user's head and body can both move together relative to the graphic. Movement of the body together with the head can be provided by a moving chair.

In some embodiments, the relative movement can be provided by moving all or a portion of a displayed graphic relative to the user and a substantially stationary display unit. In other embodiments, the graphic can be moved by movement of a display unit.

The information obtained at step 130 can include an indication of the user's perception of the orientation of the graphic, the content of the graphic, or other information. The information can be obtained via one or more input devices, such as, for example, a keyboard, a mouse, a joystick, an accelerometer, a gyroscope, and a camera. The input device(s) can be connected to a computer or other device, such as desktop computer, laptop computer, mobile phone or tablet, by a wired or wireless connection. In some embodiments, one or more of the input devices can be integrated into device such as desktop computer, laptop computer, mobile phone or tablet. Depending on the setting, the information can be provided by the user directly entering the user's perception via the input device, or the user can provide the information to a clinician or other observer who enters the user's perception via the input device. In some embodiments, the obtained information can include user's involuntary and/or unconscious indications of perception, such as head tilt relative to the body, the user's variation of head movement, etc. In some embodiments, the information obtained can include the user's report of symptoms experienced during the viewing of the graphic and relative motion. The information can further include indication of the symptoms' severity.

The modification of step 140 can include modifying one or more graphic display parameters, one or more relative movement parameter, or both. Graphic display parameters that can be modified include, for example, a size of an element, a color of an element, a degree of contrast between an element and a background, a degree of blurring or sharpening an element, an orientation of an element, a type of an element, a number of elements, a duration of presentation of an element, and other graphic display characteristics. The element can be, for example, a symbol, an icon, a part of an image, or a collection of a parts an image. In some embodiments, the element is an optotype. Relative movement parameters that can be modified include, for example, a direction of movement of one or more graphic elements, a rate of movement of one or more graphic elements, a magnitude of movement of one or more graphic elements, a direction of head movement, a rate of head movement, a magnitude of head movement, a direction of body movement, a rate of body movement, and a magnitude of body movement.

For example, if the information obtained regarding the user's perception of the graphic accurately identifies or describes the graphic, such as an orientation of the graphic or an element of the graphic, one or more graphic display parameters, one or more relative movement parameters, or both can be modified so that perception of one or more attributes of the graphic or graphic element is more difficult. For example, a graphic element can be made smaller to challenge the user. On the other hand, if the information obtained regarding the user's perception of the graphic inaccurately identifies or describes the graphic, one or more graphic display parameters, one or more relative movement parameters, or both can be modified so that perception of one or more attributes of the graphic or graphic element is facilitated. For example, a size of a graphic element can be increased. Accuracy can be a binary assessment or can be assessed with regard to a degree of accuracy.

In addition or alternative to the accuracy, one or more graphic display parameters, one or more relative movement parameters, or both can be modified based one or more of the speed of response, time until the process is terminated, and performance on the DHI. The speed of response can be, for example, an amount of time elapsed between presentation of the graphic or a graphical element to the user and the input or reception of the user's response.

In some embodiments, one or more graphic display parameters, one or more relative movement parameters, or both can be modified based on information obtained in a single response or set of responses regarding a particular presentation of a graphic to a user. In other embodiments, modifications can be based on information obtained in multiple responses or sets of responses regarding a plurality of graphical presentations to the user. For example, the user's perception of the graphic can be determined to be accurate when the user has correctly identified a specified attribute of the graphic with at least a threshold reliability over a predetermined number of iterations. As another example, the user's perception of the graphic can be determined to be accurate when the user has correctly identified a specified attribute of the graphic within a predetermined period after display of the graphic in a predetermined number of iterations.

Figure 2:
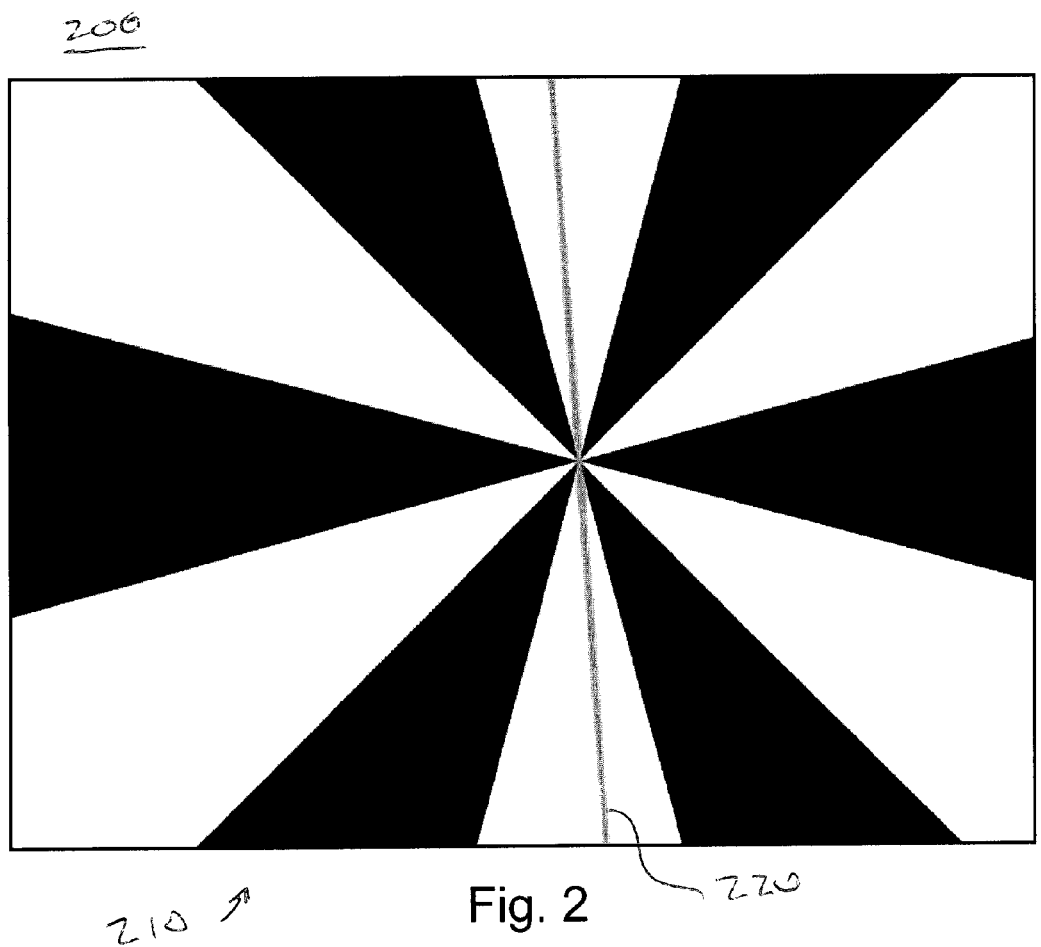
FIG. 2 illustrates an exemplary graphic according to certain aspects of the disclosure.

In some exemplary embodiments, the relative movement between the graphic and the user's head can be provided primarily by movement of the graphic, while the user's head remains static. In some such embodiments, the graphic displayed at step 100 can include a dynamic image and a static image. Movement of the dynamic image can provide the relative movement of step 120 while the user's head remains static. The dynamic image can provide the relative movement and can be any of a number of different moving fields or images. The movement of the dynamic image can be uniform rotation about a point, or movement can be variable (e.g., stars moving at different rates in a starfield). The static image can provide a reference point with reference to which the user can provide an indication of perception. For example, as illustrated in FIG. 2, the graphic 200 can comprise a dynamic image 210 (e.g., the black and white pinwheel design as illustrated) that can rotate and a static image 220 (e.g., the gray line), which the user can be directed to attempt to move to a specified orientation, such as vertical or horizontal. The line can be presented initially an orientation that is or is not already oriented in the specified manner. For example, when the user is directed to orient the line such that it appear vertical to the user, the line can be presented to the user in an orientation that is already objectively vertical or objectively non-vertical.

While a grey line 220 is shown is FIG. 2, a number of other static images can be used, including but not limited to, any bar, narrow object, cross, plus sign, star, Landolt C, or other stationary image with a directional identity suitable for comparison with a reference direction. Likewise, the reference direction is shown as vertical for illustration purposes, but could be modified to include a horizontal direction, or other orientation.

In some embodiments, a template can be placed over a display unit to prevent a bezel of the display unit from providing the user a reference for vertical and/or horizontal orientation. Such a template can comprise a body having a generally circular perimeter and a generally circular opening. The perimeter can be sufficiently large to extend around all or a majority of a bezel of a display. The circular opening can be large enough to permit viewing of the graphic, yet sufficiently small that the bezel cannot be viewed through the opening.

With the dynamic image moving, the user can be requested to provide an indication of perception of the graphic and such indication can be obtained. Thus, the information obtained at step 130 can include an indication of perceived orientation of the static image, provided either directly or indirectly by the user. Such indication can be relative to a reference direction (e.g., vertical). Perceived orientation can include indicators such as above, below, to the right, or to the left, rotated clockwise, rotated counterclockwise, pointing in a particular direction, deviated, or oriented at a particular position, etc. For example, in some embodiments where the static image is a line, the perceived orientation can include an indication that the line is perceived as either (1) vertical, (2) rotated in a first direction (e.g., clockwise) from vertical, or (3) rotated in a second direction (e.g., counterclockwise) from vertical. The indication of perception can be provided in a number of ways. For example, the user can use arrow keys of a keyboard (e.g., up, down, left, or right) to indicate the direction of orientation of the static image, or the user can attempt to correctly orient the line, providing an indication of the user's perceived orientation of the line.

In some exemplary embodiments, the relative movement between the graphic and the user's head can be provided primarily by movement of the user's head, while the graphic remains static. In some such embodiments, methods of treating vestibular disorders can include permitting movement of the user's head and determining whether the user's head movement exceeds a threshold. In some such embodiments, all or a portion of the graphic displayed at step 100 can be displayed to the user only when the user's head movement exceeds the threshold.

In such embodiments, the relative movement provided at step 120 can include movement of the user's head, resulting from the user receiving an instruction or other directive to begin head movement. In some instances, the movement of the user's head movement can result from direct manipulation of the user's head or body. Once the user's head is moving, the head movement can be measured and compared with one or more threshold values. The measurement of the head movement can involve the use of one or more gyroscopes on a headgear, counting cycles, or other means of determining the velocity, frequency, and amplitude of head movement. The measurement can be compared with minimum, maximum, or other target values or suitable ranges, such as particular velocity, frequency, and amplitude for yaw, pitch, roll, or any combination thereof. The target values for the threshold can be set at predetermined values, or the threshold can be dynamic, depending on the information regarding the user's perception. In other words, the threshold can be selected based, at least in part, on the perception information of a previously displayed graphic. The threshold can be a relative movement parameter. Once the threshold has been reached, the graphic or one or more elements of the graphic can be displayed. The graphic can include a static optotype, such as a ring having a gap (e.g., Landolt C), Tumbling E, alpha numeric character, or other character or depiction.

In some embodiments, the graphic can be displayed based on an estimate that a user's head is moving without monitoring head movement. For example, the user can be presented with a visual or auditory indication of the rate at which the head should be moved. Such a visual indication can be a part of the graphic. In some embodiments, the graphic or a graphic element can be presented after a predetermined time of presenting the movement indication or instruction to the user. In some embodiments, the graphic or a graphic element can be presented upon a user input, such as a key stroke or mouse click, signaling that the dead is moving at the prompted rate.

The information obtained at step 130 can include an indication of perceived orientation of the optotype. For example, when the optotype is a ring with a gap, the indication of perceived orientation of the optotype can include an indication of the perceived direction or location of the gap. In other embodiments, the information can include an identification of an alphanumeric character by selecting the character on a keyboard.

After the user has provided an indication of perceived orientation, identity, or other attribute of the optotype, the modification of step 140 can include moving the graphic to another location, changing the graphic to another optotype, or other modification such as those graphic display parameters identified herein. In one embodiment, if the user correctly identifies the orientation of the optotype, a more difficult optotype (in the form of blurred, smaller, etc.) is be presented to challenge the user.

After one or more graphic display parameters, one or more relative movement parameters, or both have been modified, the graphic can be modified and presented to the user, the relative movement between the user's head the graphic can be modified, or both and information regarding the user's perception of the graphic can again be obtained. Subsequently, one or more graphic display parameters, one or more relative movement parameters, or both can be modified. This process can be repeated through in a series of iterations. Information obtained from the series of iterations can be used to generate an indicator of the user's perception of the graphic. The indicator can be, for example an estimate of dynamic visual acuity of the user or a set of estimates of dynamic visual acuity of the user under different conditions. The indicator can be stored, for example in a machine-readable medium on a local system, such as a computer mobile phone, tablet, or other device, or on a remote system, such as a server. The indicator can later be retrieved for use in a subsequent series of iterations.

The subsequent series of iterations can commence approximately an hour, four hours, a day, two days, three days, a week, or other time period after conclusion of the first series. In the second series of iterations, the display of the graphic, the relative movement between the user's head and the graphic, or both can be determined or modified based on the indicator of the user's perception of the graphic generated from the information obtained in the prior series of iterations. For example, an initial value for one or more graphic display parameters, one or more relative movement parameters, or both in the second series can be determined or modified at least in part based on the indicator of the user's perception of the graphic generated from the information obtained in the prior series of iterations. Thus, in the first iteration of the second series, the graphic or an element thereof can be displayed in accordance with the a graphic display parameter based at least partially on the indicator, the relative movement between the user's head and the graphic can be prompted in accordance with a relative movement parameter based at least partially on the indicator.

In some embodiments, one or more graphic display parameters, one or more relative movement parameters, or both in the second series can be varied among iterations in a random manner.

In some embodiments, one or more graphic display parameters, one or more relative movement parameters, or both in the second series can be varied among iterations in a manner that may appear random to the user but include a relatively larger number of values of the varied parameters that are near the limits of the user's ability than values that are well within or outside of the user's ability.

In some embodiments, based on one or more indicators, an presentation of a graphic and relative movement between the user's head the and graphic during an initial iteration can be based on graphic display parameters and relative movement parameters that are selected, based on one or more indicators, to be well within the ability of the user can be progressively modified through subsequent iterations in the same series to become more difficult if the user's results indicate at least a threshold ability to perceive the graphic, as discussed above for example. In some such embodiments, a relatively large number of iterations can be based on graphic display parameters and relative movement parameters that are selected, based on one or more indicators, to be slightly within or slightly beyond the user's ability.

In some embodiments, information obtained in the subsequent series of iterations can be used to generate another indicator of the user's perception of the graphic or modify the prior indicator. In some embodiments, one or more graphic display parameters, one or more relative movement parameters, or both can be modified based on a plurality of indicators generated during a plurality of series of iterations.

Series of iterations can be repeated to treat a vestibular disorder over a period of days, weeks, months, or years. Series of iterations can be performed on a daily, semi-daily, bi-daily, weekly, semi-weekly, weekly, or other frequency. The period between series can be varies depending on the severity of the vestibular disorder, discomfort of the user, and responsiveness of the user to treatment, among other considerations.

Figure 3:
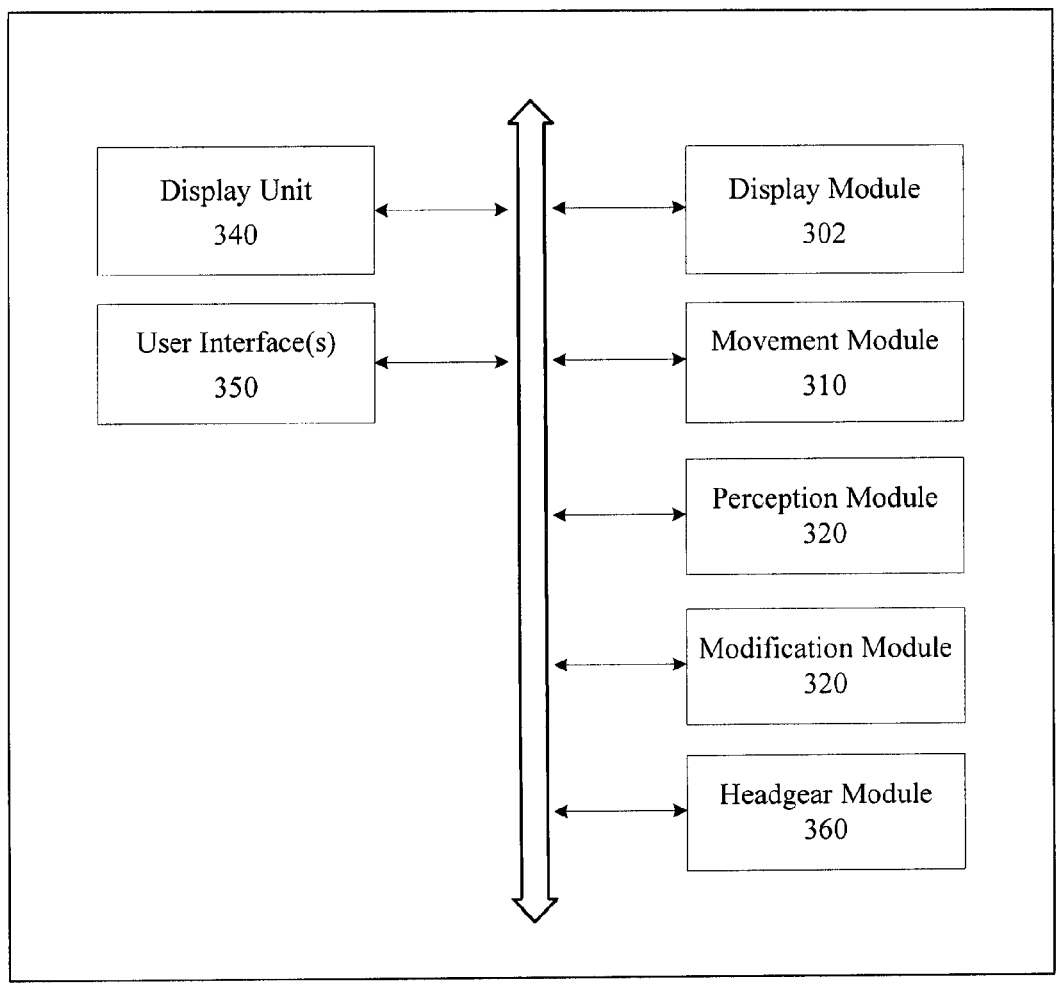
FIG. 3 is a block diagram illustrating an exemplary system for treating vertigo using a displayed graphic.

Various systems can be used to treat vertigo in accordance with the methods of the present disclosure, including both hardware and software. For example, as illustrated in FIG. 3, such a system 300 can include a display module 302, a movement module 310, a perception module 320, and a modification module 330. The display module 302 can be configured to facilitate, by a processor, displaying a graphic. The movement module 310 can be configured to facilitate, by a processor, providing relative movement between the graphic and a user's head while the user views the graphic, so as to induce vertigo symptoms. The perception module 320 can be configured to receive, by a processor, information regarding the user's perception of the graphic. The modification module 330 can be configured to facilitate, by a processor and responsive to the obtained information, modifying at least one of the graphic and a relative movement between the graphic and the user's head.

In some embodiments, a computer display 340 can be configured to display the graphic and a user interface 350 can be configured to receive the information indicative of the user's perception of the graphic. In some embodiments, the user interface 350 includes at least one of a keyboard, a computer mouse, a button, and a joystick.

The systems of the present disclosure can be used in instances where the graphic moves. In one embodiment, users can be given a login name for a web-based application, and can be prompted to enter set up information such as the size and viewing distance of their computer monitor. The web-based application can test normal controls, those with unilateral vestibulopathy, and MAV. The monitor can initially display a blank background, and the user can be prompted to orient a line with subjective vertical using the arrow keys which can change the line orientation using a staircase. The line can be blurred to prevent correct orientation from close examination of pixels. As the test progresses, more complex stimuli can be presented, including busy high contrast backgrounds, flashing elements, rotation, and/or vection. The user can exit testing at any time, for example, by pressing the space bar if the stimuli become uncomfortable. Performance measures can be remotely monitored and can include a variety of readings, including but not limited to, time spent, line orientation, number of adjustments made, and the user's level of annoyance with the stimulus. Users can be prompted to complete the test daily so that performance can be monitored over time. Users can complete an electronic version of the DHI on a periodic basis so that symptoms can be monitored.

Figure 4:
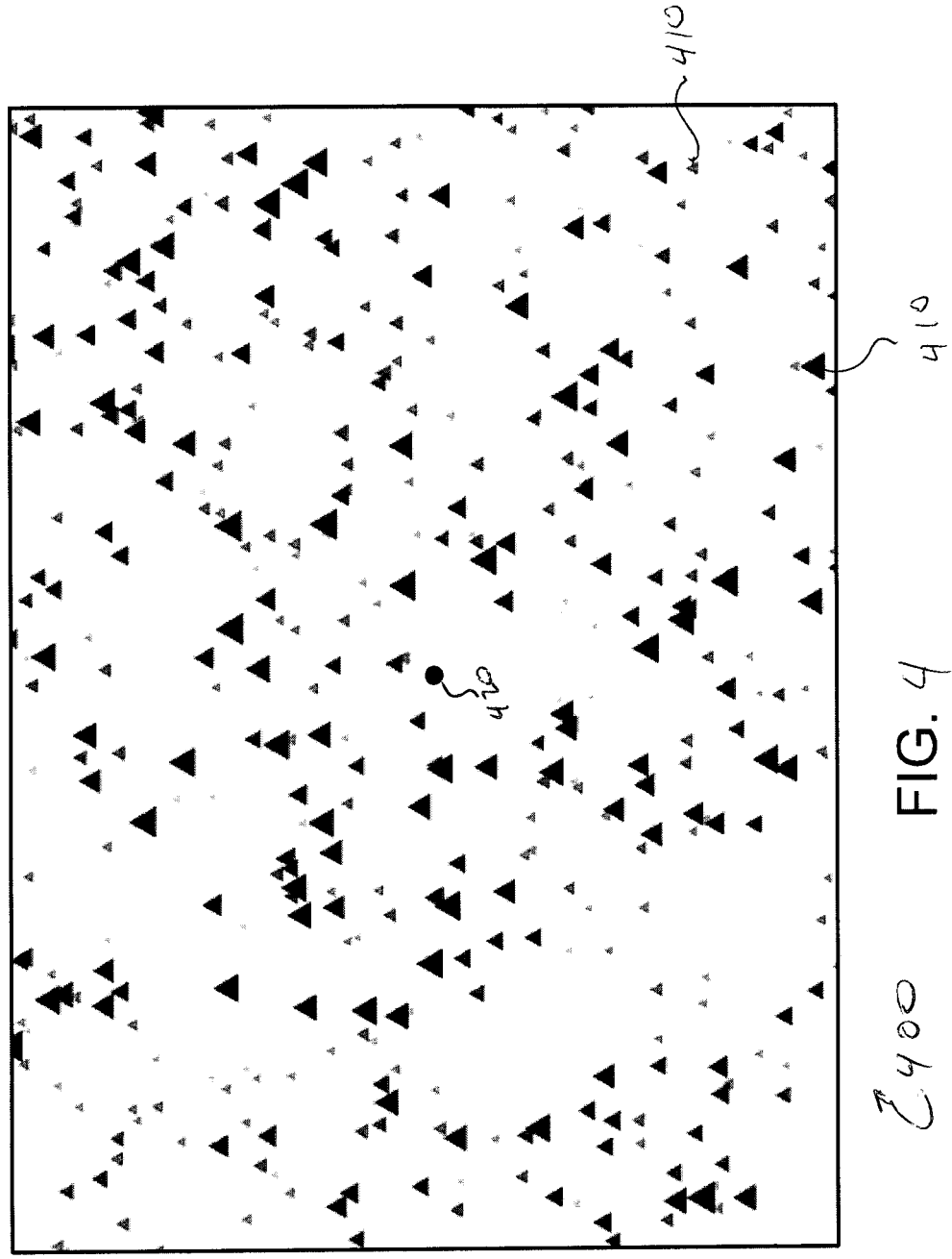
FIG. 4 illustrates an exemplary graphic according to certain aspects of the disclosure.

Visual optic flow stimuli can be bothersome to MAV patients, even though their heading perception does not appear to be impaired. However, comparison of two visual motion stimuli can be impaired in MAV patients. A starfield or other stimulus can provide a representation of a 3D environment. For example, as illustrated in FIG. 4, the user can be presented a visual field 400 of dots 410 having size and motion designed to represent a 3D environment. The dots (represented as triangles in the illustration) can each have a limited lifespan and some independent motion to prevent landmarks from being identified. The dots can move in two or more intervals to simulate translation or rotation of the environment relative to the user. The user can identify which movement is larger and the intervals of motion can be adjusted until reaching the point of subjective equality (PSE) (i.e., where the user has an equal probability of identifying the first or second interval as larger). MAV can be associated with larger differences in first and second intervals and more errors in identifying differences. A stationary fixation point 420 can be provided, such as the circle located in the center of FIG. 4, for example. The method can be delivered in a web-based method and can be used for remote testing and rehabilitation. The responses and test parameters can be remotely recorded on a server.

Repeated exposure to visual motion stimuli can improve visual vertigo symptoms common in MAV. Thus, patients with MAV can be able to build up to more dynamic motion stimuli over time, and tolerance of these stimuli can improve their symptoms in everyday situations. Some user's may respond better to rehabilitation by repeated exposure to visual motion stimuli than others. When response improves, visual stimuli can be presented at increasingly challenging levels (e.g., increasing velocity, contrast, number of stimuli, etc.). Over time, the user can view progressively more challenging stimuli as determined by performance. In individuals with MAV or other persons with vertigo, the stimuli can be modified for maximum effectiveness, including the use of additional rehabilitation tasks such as dynamic visual acuity (i.e., measuring visual acuity during head movement). Although dynamic visual acuity has been shown to be a good clinical test of vestibular function, it has been difficult to perform in most clinical situations because patients tend to decrease head motion to allow better visualization. One way to ensure standard head motion can be to have the user move with a bar on the screen or only show the target when a sensor worn on the head determines that the head is moving quickly enough.

Figure 8:
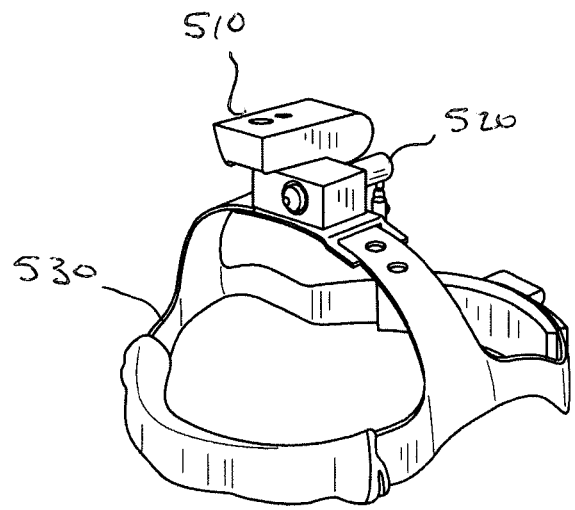
FIG. 8 illustrates headgear according to an embodiment.

Referring again to FIG. 3, in instances where the user's head moves, the system can include a headgear module 360 to ensure movement of the user's head in excess of a threshold prior to displaying the graphic. More particularly, the headgear module 360 can be configured to (1) facilitate, by a processor, requesting movement of the user's head, so as to provide the relative movement between the graphic and the user's head, (2) receive, by a processor, information regarding movement of the user's head, (3) facilitate, by a processor, determining whether the user's head movement exceeds a threshold, and (4) facilitate, by a processor and responsive to the obtained information, displaying the graphic only when the user's head movement exceeds the threshold. The headgear module 360 can communicate with a headgear 800, such as shown in FIG. 8 for example, for measuring head movement, such as velocity and acceleration. The headgear can comprise a head velocity sensor 510, a calibration laser 520, and a headband 530. The calibration laser, where present, can be used to calibrate the device by aiming it at a moving dot on the screen. The head velocity sensor can be connected to the system by a wired or wireless connection. Wireless connection can be provided by via a wireless network, including Bluetooth or other similar technology. In some embodiments, the sensor can be integrated into a mobile device, such as a phone for example, that can be selectively attached to the headband 530.

Figure 10:
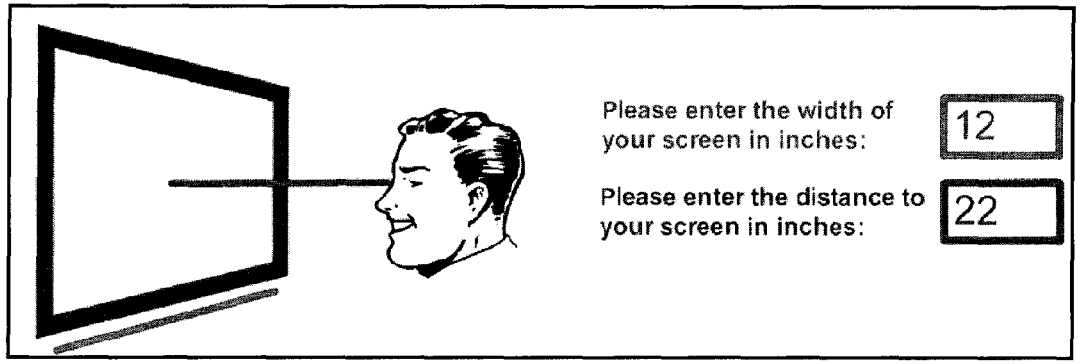
FIG. 10 illustrates a calibration instruction and input requests according to an embodiment.

As with the example setting forth a web-based application for testing and improving MAV via moving images, the use of a web-based application to monitor head movement in the performance of a DVA task can be for use in vestibular rehabilitation. The application can gather some basic information from the user such as the size of the screen and the viewing distance. For example, information can be obtained at least in part through display of a request such as illustrated in FIG. 10 and input from the user any input means. The application can also gather information on the resolution of the users computer screen as well as the speed, and the operating system.

Figure 9:
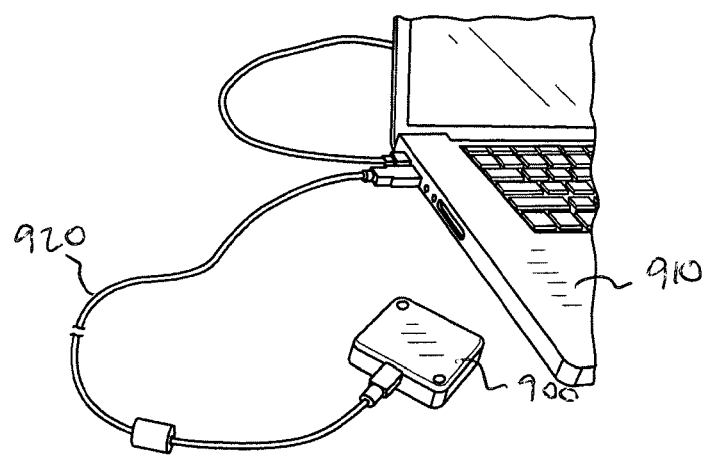
FIG. 9 illustrates a device, according to an embodiment, comprising one or more sensors.

During testing the motion of the user's head can be monitored via a sensor worn on the user's head. The sensor can report the user's angular head velocity to the computer. In one embodiment, a wireless device can act as a mouse to move a pointer. The device can be calibrated using a laser which can be aimed at a moving dot on the user's screen. Such a calibrated device may not require any additional drivers to be installed on the user's computer. However, such a device may require calibration on the user's computer, which may be difficult for some to accomplish. Further, the mouse pointer may have difficulty encoding change if the pointer reaches the edge of the screen. Thus, in another embodiment, the device can directly report angular head angular velocity (in yaw, pitch, or roll) as measured by one or more internal gyroscopes and transmitted via a universal serial bus (USB) connection. Such a device may require a driver to be installed on the user's computer, but may provide superior head rotation monitoring without the need for calibration by the user. FIG. 9 illustrates a device 900 connected to a computer 910 via a USB cable 920. In addition to the devices described above, head velocity can be measured by other devices and/or techniques including optical techniques using video cameras to monitor the position of points fixed to the head, such techniques are currently popular for video game consoles.

Figure 11:
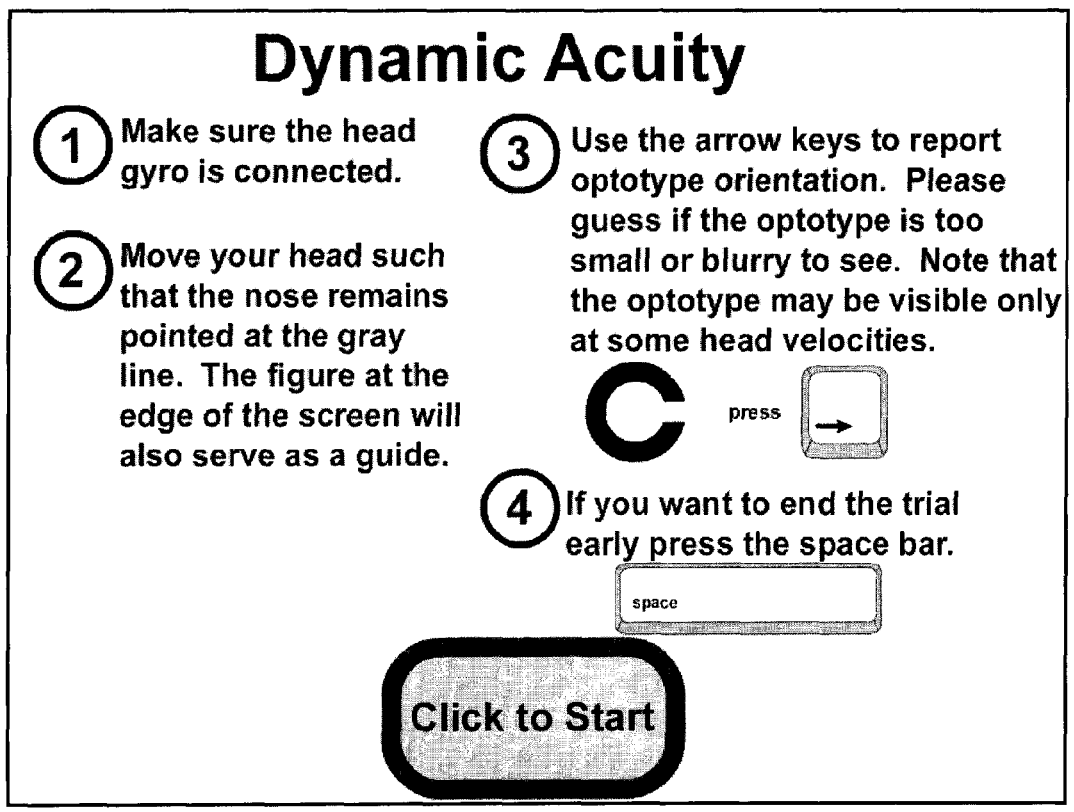
FIG. 11 illustrates task performance instructions according to an embodiment.

The user can be given brief instruction on how to move their head and report the orientation of a visual optotype, such as shown for example in FIG. 11. The user can indicate understanding of the instruction by pressing a button or otherwise providing feedback.

Figure 5:
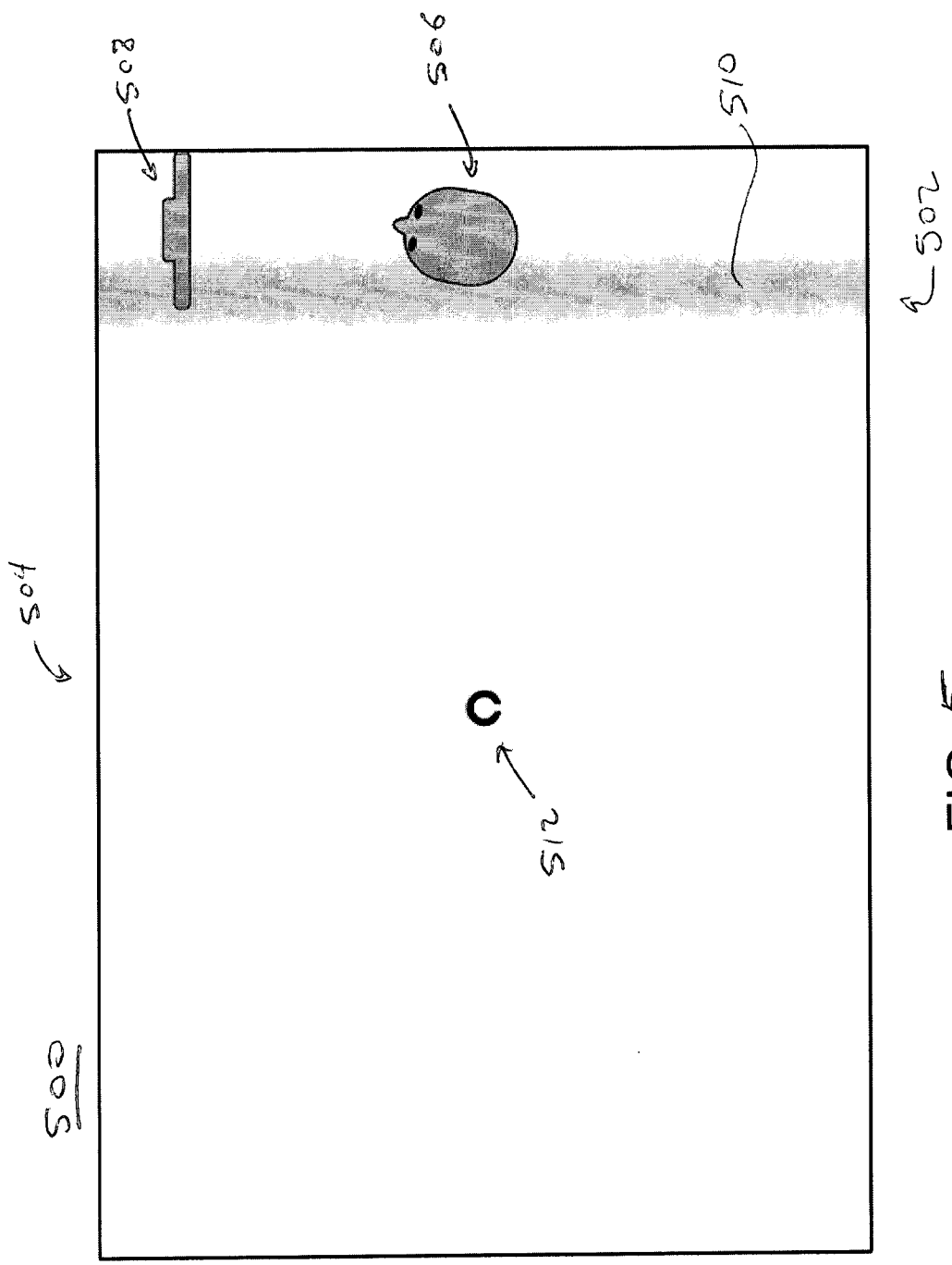
FIG. 5 illustrates a screen showing an exemplary graphic according to certain aspects of the disclosure.

Referring to FIG. 5, a graphic 500 on one side 502 of the screen 504 can demonstrate how the user should move their head relative to the screen 504. The graphic 500 can include a representation of a head 506 and a representation of a screen 508. The representation of the head 506 can rotate at a desired frequency and peak velocity. Simultaneously, a graphic (e.g., the grey bar 510) can move back and forth across the screen 504 to demonstrate the direction the user's head should be pointed at a particular instant. The bar 510 may not always be visible as the user's head may sometimes not be pointed at the screen 504 when the stimulus is large. A metronome style audible click can also be used to mark the points when the user's head should reach the extreme limit of rotation. If the head velocity cannot be regularly achieved it can be decreased as required. In the center of the screen 504 an optotype 512 such as a Landolt C can be displayed when the head is moving faster than a minimum velocity. The velocity threshold can be determined by the user's condition, their progress in therapy and their prior responses. The velocity threshold can be direction specific in some situations, i.e., only appear when the head is moving to the right or to the left. This can be helpful in rehabilitating unilateral vestibular loss which head movement towards the side of the lesion tends to be selectively impaired.

The optotype or other graphic element can be displayed for a brief period. For example, the optotype or other graphic element can be displayed for 10 ms, 16 ms, 20 ms, 40 ms, 60 ms, 80 ms, or approximately any of those times. Preferably the time that the optotype or other graphic element is displayed is less than 100 ms as other visual systems begin contributing to the user's perception and compensating for vestibular deficiency. Depending on the display unit used, the ability to display the optotype or other graphic element may be affected by the display unit's refresh rate. An appropriately large duration can be selected to ensure the that the optotype or other graphic element is presented to the user.

Once the optotype 512 is visible, its orientation (e.g., the direction in which the gap "points") can be reported using arrow keys, or other buttons or inputs. If there is no response or if the response is incorrect the optotype 512 can be modified to enhance clarity (e.g., the size of the C can grow). If the responses are correct, the optotype 512 can be modified to reduce clarity (e.g., the size of the C can decrease). In this way a performance threshold can be determined, while the user practices doing the task which can be of rehabilitative value. Because it can be a web-based application the user's participation and performance can be monitored with the parameters remotely adjusted as needed. The user can also receive a score which they can use to get objective measures of improvement over time.

It should be noted that while relative movement between the graphic and the user's head is described as movement of the graphic or movement of the user's head, the two types of movements could be used together to either enhance, or reduce the vertigo inducing effect. Further, the use of the term "static" is not intended to be limited to completely still without any movement whatsoever. Rather, it is intended that "static" mean "substantially stationary" or having little or no movement perceivable by the user.

The methods and systems disclosed herein can be applied to treatment of otolith disorders. In some such embodiments, movement of the head can comprise translation in addition or alternative to rotation.

Figure 6:
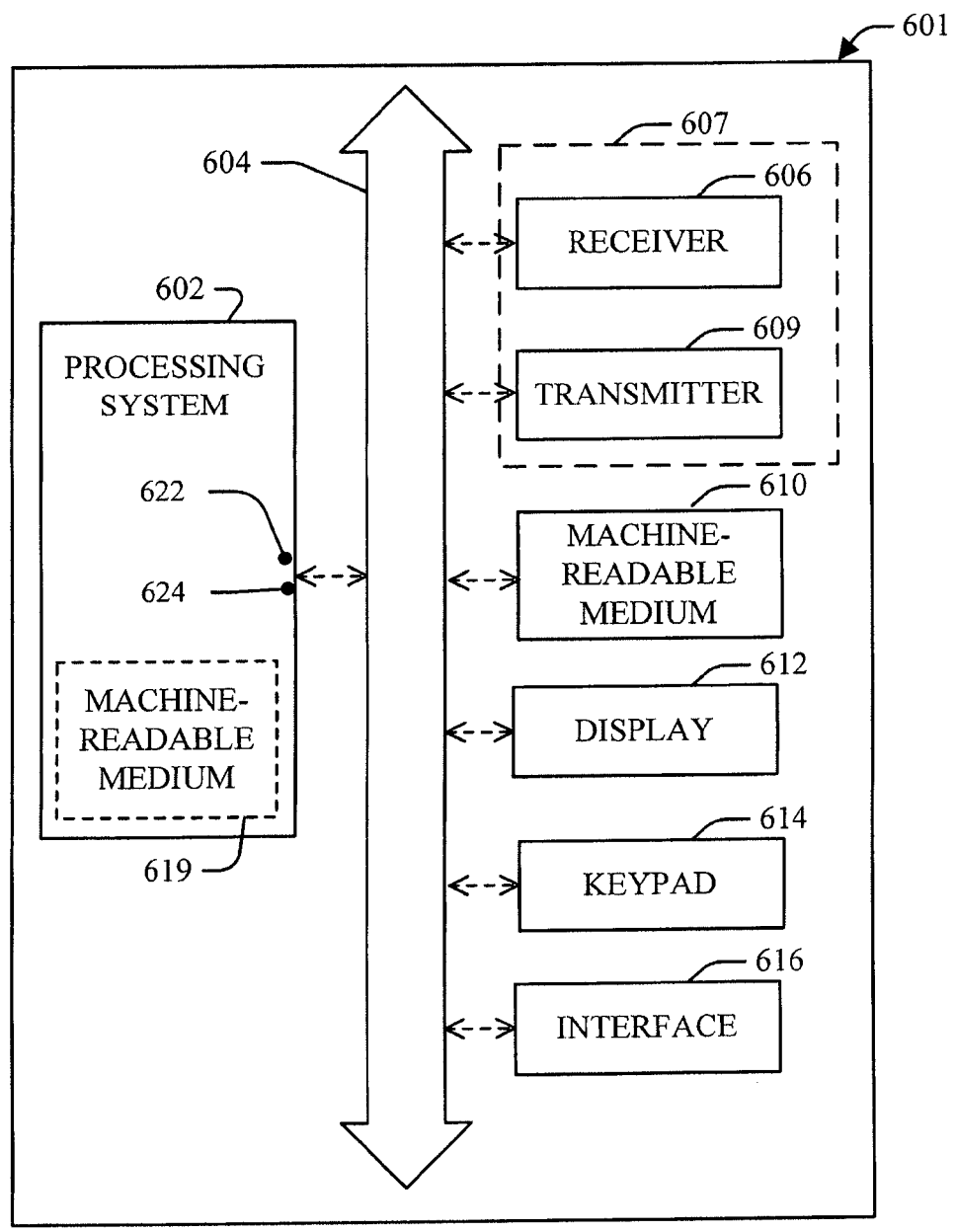
FIG. 6 is a block diagram illustrating an exemplary computer system with which the methods and systems of the present disclosure can be implemented.

FIG. 6 is a conceptual block diagram illustrating an example of a system, in accordance with various aspects of the subject technology. A system 601 can be, for example, a client device or a server. The system 601 may include a processing system 602. The processing system 602 is capable of communication with a receiver 606 and a transmitter 609 through a bus 604 or other structures or devices. It should be understood that communication means other than busses can be utilized with the disclosed configurations. The processing system 602 can generate audio, video, multimedia, and/or other types of data to be provided to the transmitter 609 for communication. In addition, audio, video, multimedia, and/or other types of data can be received at the receiver 606, and processed by the processing system 602.

The processing system 602 may include a processor for executing instructions and may further include a machine-readable medium 619, such as a volatile or non-volatile memory, for storing data and/or instructions for software programs. The instructions, which may be stored in a machine-readable medium 610 and/or 619, may be executed by the processing system 602 to control and manage access to the various networks, as well as provide other communication and processing functions. The instructions may also include instructions executed by the processing system 602 for various user interface devices, such as a display 612 and a keypad 614. The processing system 602 may include an input port 622 and an output port 624. Each of the input port 622 and the output port 624 may include one or more ports. The input port 622 and the output port 624 may be the same port (e.g., a bi-directional port) or may be different ports.

The processing system 602 may be implemented using software, hardware, or a combination of both. By way of example, the processing system 602 may be implemented with one or more processors. A processor may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device that can perform calculations or other manipulations of information.

A machine-readable medium can be one or more machine-readable media. Software shall be construed broadly to mean instructions, data, or any combination thereof, whether referred to as software, firmware, middleware, microcode, hardware description language, or otherwise. Instructions may include code (e.g., in source code format, binary code format, executable code format, or any other suitable format of code).

Machine-readable media (e.g., 619) may include storage integrated into a processing system, such as might be the case with an ASIC. Machine-readable media (e.g., 610) may also include storage external to a processing system, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device. Those skilled in the art will recognize how best to implement the described functionality for the processing system 602. According to one aspect of the disclosure, a machine-readable medium is a computer-readable medium encoded or stored with instructions and is a computing element, which defines structural and functional interrelationships between the instructions and the rest of the system, which permit the instructions' functionality to be realized. In one aspect, a machine-readable medium is a non-transitory machine-readable medium, a machine-readable storage medium, or a non-transitory machine-readable storage medium. In one aspect, a computer-readable medium is a non-transitory computer-readable medium, a computer-readable storage medium, or a non-transitory computer-readable storage medium. Instructions may be executable, for example, by a client device or server or by a processing system of a client device or server. Instructions can be, for example, a computer program including code.

An interface 616 may be any type of interface and may reside between any of the components shown in FIG. 6. An interface 616 may also be, for example, an interface to the outside world (e.g., an Internet network interface). A transceiver block 607 may represent one or more transceivers, and each transceiver may include a receiver 606 and a transmitter 609. A functionality implemented in a processing system 602 may be implemented in a portion of a receiver 606, a portion of a transmitter 609, a portion of a machine-readable medium 610, a portion of a display 612, a portion of a keypad 614, or a portion of an interface 616, and vice versa.

Figure 7:
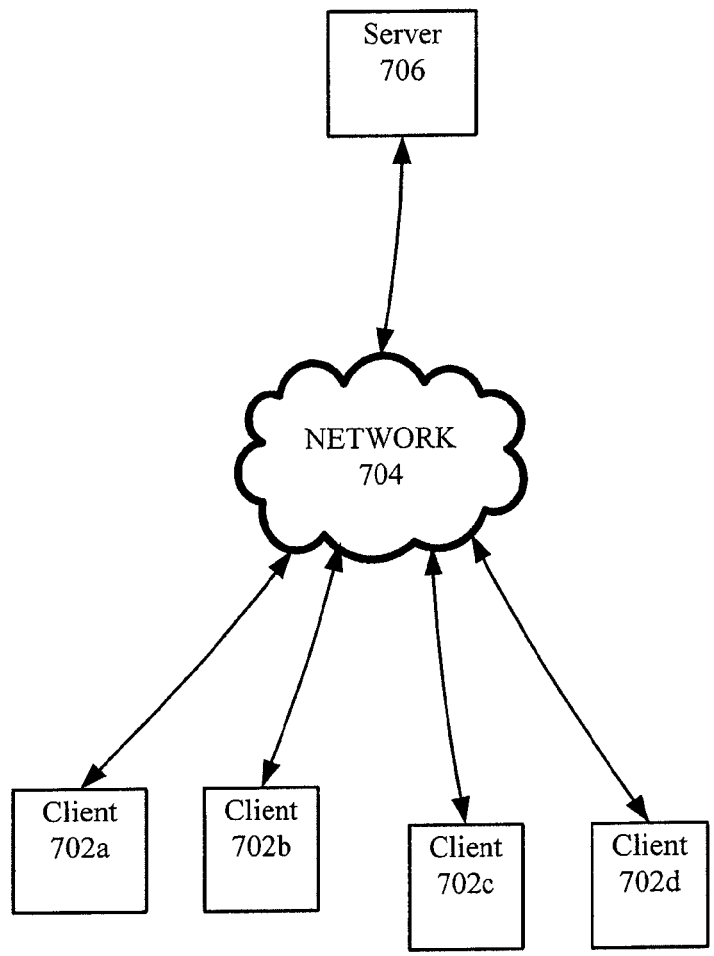
FIG. 7 is a block diagram illustrating an exemplary computer network system.

FIG. 7 illustrates a simplified diagram of a system 700, in accordance with various embodiments of the subject technology. The system 700 may include one ore more remote client devices 702 (e.g., client devices 702a, 702b, 702c, and 702d) in communication with a server computing device 706 (server) via a network 704. In some embodiments, the server 706 is configured to run applications that may be accessed and controlled at the client devices 702. For example, a user at a client device 702 may use a web browser to access and control an application running on the server 706 over the network 704. In some embodiments, the server 706 is configured to allow remote sessions (e.g., remote desktop sessions) wherein users can access applications and files on the server 706 by logging onto the server 706 from a client device 702. Such a connection may be established using any of several well-known techniques such as the Remote Desktop Protocol (RDP) on a Windows-based server.

By way of illustration and not limitation, in one aspect of the disclosure, stated from a perspective of a server side (treating a server as a local device and treating a client device as a remote device), a server application is executed (or runs) at a server 706. While a remote client device 702 may receive and display a view of the server application on a display local to the remote client device 702, the remote client device 702 does not execute (or run) the server application at the remote client device 702. Stated in another way from a perspective of the client side (treating a server as remote device and treating a client device as a local device), a remote application is executed (or runs) at a remote server 706.

By way of illustration and not limitation, a client device 702 can represent a computer, a mobile phone, a laptop computer, a thin client device, a personal digital assistant (PDA), a portable computing device, or a suitable device with a processor. In one example, a client device 702 is a smartphone (e.g., iPhone, Android phone, Blackberry, etc.). In certain configurations, a client device 702 can represent an audio player, a game console, a camera, a camcorder, an audio device, a video device, a multimedia device, or a device capable of supporting a connection to a remote server. In one example, a client device 702 can be mobile. In another example, a client device 702 can be stationary. According to one aspect of the disclosure, a client device 702 may be a device having at least a processor and memory, where the total amount of memory of the client device 702 could be less than the total amount of memory in a server 706. In one example, a client device 702 does not have a hard disk. In one aspect, a client device 702 has a display smaller than a display supported by a server 706. In one aspect, a client device may include one or more client devices.

In some embodiments, a server 706 may represent a computer, a laptop computer, a computing device, a virtual machine (e.g., VMware® Virtual Machine), a desktop session (e.g., Microsoft Terminal Server), a published application (e.g., Microsoft Terminal Server) or a suitable device with a processor. In some embodiments, a server 706 can be stationary. In some embodiments, a server 706 can be mobile. In certain configurations, a server 706 may be any device that can represent a client device. In some embodiments, a server 706 may include one or more servers.

In one example, a first device is remote to a second device when the first device is not directly connected to the second device. In one example, a first remote device may be connected to a second device over a communication network such as a Local Area Network (LAN), a Wide Area Network (WAN), and/or other network.

When a client device 702 and a server 706 are remote with respect to each other, a client device 702 may connect to a server 706 over a network 704, for example, via a modem connection, a LAN connection including the Ethernet or a broadband WAN connection including DSL, Cable, T1, T3, Fiber Optics, Wi-Fi, or a mobile network connection including GSM, GPRS, 3G, WiMax or other network connection. A network 704 can be a LAN network, a WAN network, a wireless network, the Internet, an intranet or other network. A network 704 may include one or more routers for routing data between client devices and/or servers. A remote device (e.g., client device, server) on a network may be addressed by a corresponding network address, such as, but not limited to, an Internet protocol (IP) address, an Internet name, a Windows Internet name service (WINS) name, a domain name or other system name. These illustrate some examples as to how one device may be remote to another device. But the subject technology is not limited to these examples.

According to certain embodiments of the subject technology, the terms "server" and "remote server" are generally used synonymously in relation to a client device, and the word "remote" may indicate that a server is in communication with other device(s), for example, over a network connection(s).

According to certain embodiments of the subject technology, the terms "client device" and "remote client device" are generally used synonymously in relation to a server, and the word "remote" may indicate that a client device is in communication with a server(s), for example, over a network connection(s).

In some embodiments, a "client device" may be sometimes referred to as a client or vice versa. Similarly, a "server" may be sometimes referred to as a server device or vice versa.

In some embodiments, the terms "local" and "remote" are relative terms, and a client device may be referred to as a local client device or a remote client device, depending on whether a client device is described from a client side or from a server side, respectively. Similarly, a server may be referred to as a local server or a remote server, depending on whether a server is described from a server side or from a client side, respectively. Furthermore, an application running on a server may be referred to as a local application, if described from a server side, and may be referred to as a remote application, if described from a client side.

In some embodiments, devices placed on a client side (e.g., devices connected directly to a client device(s) or to one another using wires or wirelessly) may be referred to as local devices with respect to a client device and remote devices with respect to a server. Similarly, devices placed on a server side (e.g., devices connected directly to a server(s) or to one another using wires or wirelessly) may be referred to as local devices with respect to a server and remote devices with respect to a client device.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

Figure 12:
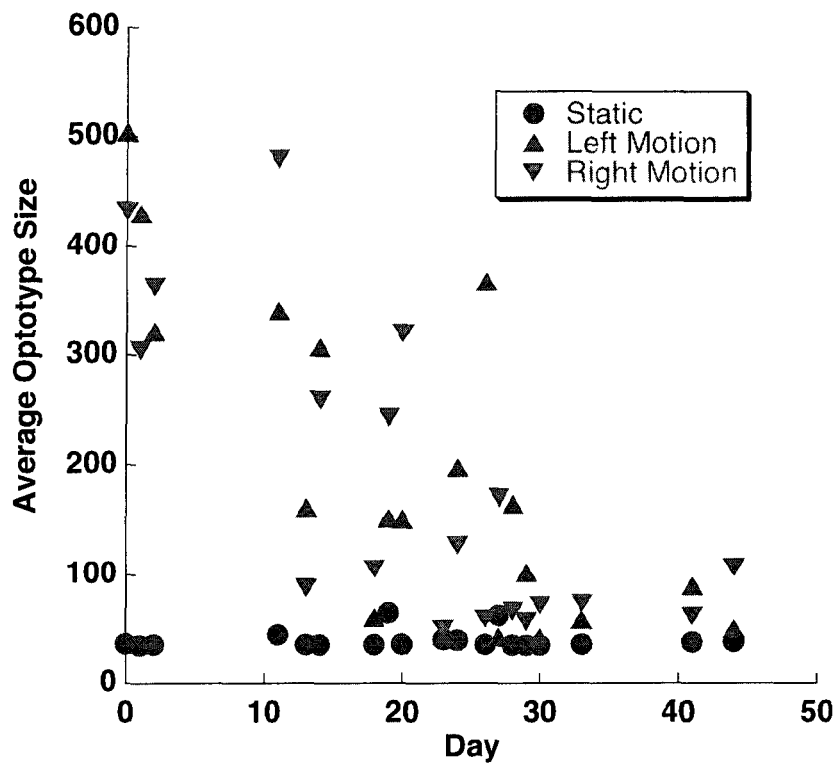
FIG. 12 illustrates average optotype size during visual acuity testing according to an embodiment.

FIG. 12 shows test data indicating that use of a web-based vestibular rehabilitation system improved both the user's symptoms and performance on the task. In FIG. 12, the vertical axis indicates average optotype (in this case a Landolt-C) size during visual acuity testing. A value of "20" represents the smallest size that can reliably be identified in a person with normal vision (i.e., 20/20). Larger numbers represent larger optotypes and worse performance. In FIG. 12, the upwardly pointing triangles indicate performance during leftward rotating motion, the downwardly pointing triangles indicate performance during rightward rotating motion, and the circles indicate static performance (no motion or substantially no motion). The size of the optotype which a user with vestibular neuronitis could reliably identify while rotating their head decreased with time as the user practiced with the device. Visual acuity measured with the head still did not improve over time indicating that the improvement of dynamic visual acuity was not merely an effect of practice with the device.

Figure 13:
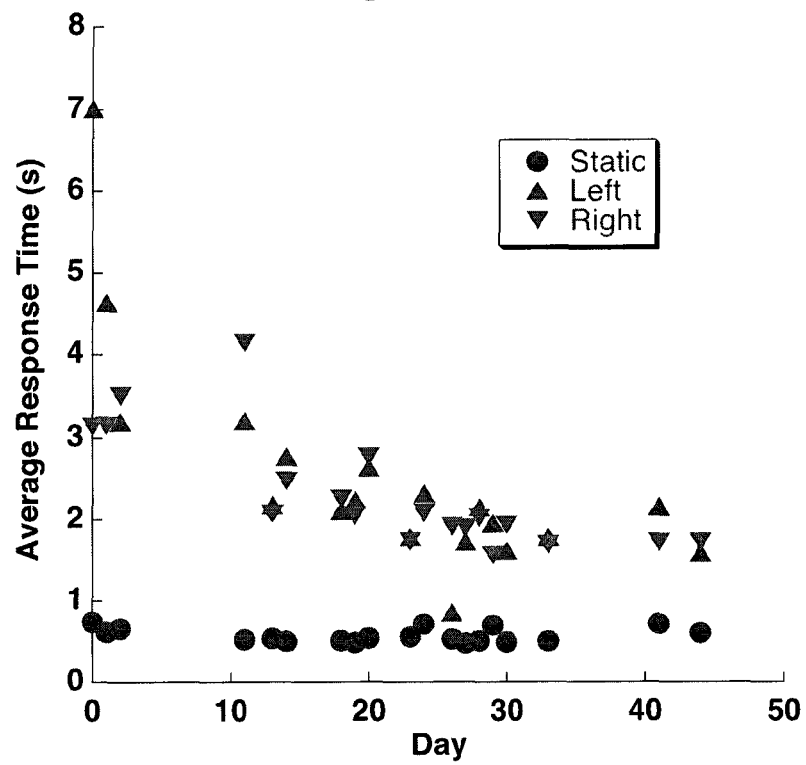
FIG. 13 illustrates average response time required to complete visual acuity tasks during testing according to an embodiment.

FIG. 13 shows test data indicating the time the user took identifying the orientation of each optotype also improved with completing of the task in the conditions in which head rotation was required. In FIG. 13, the vertical axis indicates the average response time required to complete each dynamic visual acuity task. Similar to FIG. 12, in FIG. 13 the upwardly pointing triangles indicate performance during leftward rotating motion, the downwardly pointing triangles indicate performance during rightward rotating motion, and the circles indicate static performance (no motion or substantially no motion). The time required to identify the static target did not change with time indicating the dynamic effect was not merely due to practice with the task but demonstrated real improvement in vestibular function.

Figure 14:
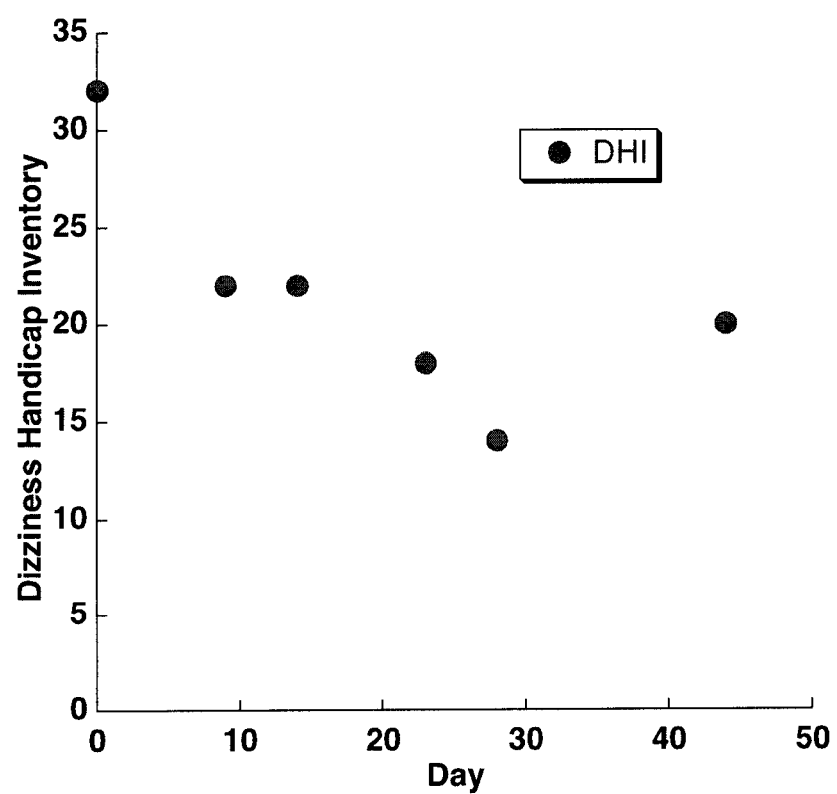
FIG. 14 illustrates Dizziness Handicap Inventory assessed during rehabilitation therapy according to an embodiment.

A concurrent improvement in function was verified with the dizziness handicap inventory (DHI) as shown in FIG. 14, measured while the subject completed the vestibular rehabilitation task. The subject was asked to complete the survey every week while doing the vestibular rehabilitation task. The score can range from 100 (most severe disability) to 0 (no disability). In this subject there was a downward trend in this measure which paralleled the improvement in performance indicated in FIGS. 12 and 13. The slight upward trend at the last point may have been influenced by the user's wife having a baby just prior to the final DHI assessment.

In a test of visual vertical determination in a total of 15 normal subjects who ranged in age from 23 to 61 (mean 40), visual vertical determination, such as described above in connection with FIG. 2, was performed with a blank background as well as moving and rotating backgrounds. The control subjects were able to accurately orient a graphic element to an average 0.5° across conditions. This test demonstrated no effect of age but all subjects had a significantly greater deviation from vertical (p<0.01) when there was a rotating background stimulus when compared with a static background. In patients with migraine associated vertigo the average deviation from vertical was 1.49° which was significantly greater than the control group (p<0.001). For migraine patients that continued with the task the deviation improved to 0.7° which is near the normal range. These results indicate that migraine patients who continued to use the system experienced improvement.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A system for treating a vestibular disorder, comprising:
one or more processors;
one or more non-transitory machine-readable media storing modules for execution by a processor, the modules comprising:
    a display module configured to facilitate, by a processor, displaying a graphic;
    a movement module configured to facilitate, by a processor, prompting relative movement between the graphic and a user's head;
    a perception module configured to receive, by a processor, information regarding the user's perception of the graphic;
    a modification module configured (a) to facilitate, by a processor and responsive to the obtained information, modifying at least one of a graphic display parameter and a relative movement parameter, (b) to facilitate, by a processor and based on the obtained information, generating at least a first indicator of the user's perception of the graphic and modifying, based at least in part on the first indicator, at least one of (i) a graphic display parameter affecting the displaying of the graphic at least one day after generation of the first indicator and (ii) a relative movement parameter affecting the prompting of relative movement at least one day after generation of the first indicator; and a monitor module configured to:

receive, by a processor, information regarding movement of the user's head;

facilitate, by a processor, determining whether the user's head movement exceeds a threshold in a direction toward a side, of the head, having a vestibular lesion associated with unilateral vestibular impairment; and facilitate, by a processor and responsive to the obtained information, displaying at least a portion of the graphic only when the user's head movement exceeds the threshold in the direction.

2. The system of claim 1, further comprising:

a display device configured to display the graphic; and a user interface configured to receive the information indicative of the user's perception of the graphic.

3. The system of claim 1, wherein the display device comprises at least one of a computer display, a television display, and a mobile device display, and the user interface comprises at least one of a keyboard, a computer mouse, a button, and a joystick.

4. The system of claim 1, wherein the monitor module is a headgear module.

5. The system of claim 1, wherein the threshold is selected based, at least in part, on the perception information of a previously displayed graphic.

6. The system of claim 1:

wherein the graphic image comprises a static optotype; and wherein the perception information comprises an indication of perceived orientation of the optotype.

7. The system of claim 6:

wherein the optotype comprises a ring having a gap; and wherein the indication of perceived orientation of the optotype comprises an indication of perceived direction of the gap.

* * * * *